United States Patent
Graham et al.

(10) Patent No.: US 10,179,094 B2
(45) Date of Patent: Jan. 15, 2019

(54) FOAMING SKINCARE FORMULATIONS

(71) Applicant: MSD Consumer Care, Inc., Memphis, TN (US)

(72) Inventors: Heidi Naomi Graham, Cordova, TN (US); Thomas A. Meyer, Germantown, TN (US); Stephen E. Baldwin, Germantown, TN (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 14/034,802

(22) Filed: Sep. 24, 2013

(65) Prior Publication Data

US 2014/0120039 A1    May 1, 2014

Related U.S. Application Data

(60) Provisional application No. 61/706,498, filed on Sep. 27, 2012.

(51) Int. Cl.
| | |
|---|---|
| *A61K 9/12* | (2006.01) |
| *A61K 8/04* | (2006.01) |
| *A61K 8/19* | (2006.01) |
| *A61K 8/365* | (2006.01) |
| *A61Q 17/04* | (2006.01) |
| *A61Q 19/00* | (2006.01) |
| *A61K 9/00* | (2006.01) |

(52) U.S. Cl.
CPC .............. *A61K 8/046* (2013.01); *A61K 8/19* (2013.01); *A61K 8/365* (2013.01); *A61K 9/0014* (2013.01); *A61Q 17/04* (2013.01); *A61Q 19/00* (2013.01); *A61K 2800/222* (2013.01); *A61K 2800/87* (2013.01)

(58) Field of Classification Search
CPC .. A61K 47/10; A61K 8/345; A61K 2800/222; A61K 2800/87; A61K 31/22; A61K 36/02; A61K 36/185; A61K 8/375; A61K 8/92; A61K 8/927; A61K 8/988; A61K 9/0018; A61K 9/06; A61K 9/282; A61K 2800/10; A61K 2800/31; A61K 2800/782; A61Q 17/04; A61Q 19/00; A61Q 15/00; A61Q 17/00; A61Q 17/005; A61Q 19/002; A61Q 19/005; A61Q 19/007; A61Q 5/00; A61Q 5/10; A61Q 9/04; A61Q 9/008; A61Q 5/06
USPC .................................................... 424/45, 70.9
See application file for complete search history.

(56) References Cited

U.S. PATENT DOCUMENTS

| | | | |
|---|---|---|---|
| 3,330,730 A | 7/1967 | Hernaadez | |
| 3,970,584 A * | 7/1976 | Hart et al. | ...................... 516/10 |
| 4,421,739 A | 12/1983 | Bouillon et al. | |
| 5,322,683 A | 6/1994 | Mackles et al. | |
| 6,143,282 A * | 11/2000 | Hansenne et al. | .............. 424/59 |
| 6,231,837 B1 | 5/2001 | Stroud et al. | |
| 6,261,541 B1 | 7/2001 | Karpov et al. | |
| 6,436,376 B1 | 8/2002 | Hansenne et al. | |
| 6,482,397 B1 | 11/2002 | Scott et al. | |
| 6,858,200 B2 | 2/2005 | Fowler | |
| 7,097,828 B2 | 8/2006 | Meyer et al. | |
| 7,244,416 B2 | 7/2007 | Meyer et al. | |
| 7,270,802 B2 | 9/2007 | Loghman-Adham | |
| 2004/0202618 A1 | 10/2004 | Riedel et al. | |
| 2004/0241105 A1 | 12/2004 | Riedel et al. | |
| 2005/0042287 A1 * | 2/2005 | Chaussee et al. | ............ 424/466 |
| 2005/0079142 A1 | 4/2005 | Brunckhorst et al. | |
| 2008/0138894 A1 | 6/2008 | Maertens et al. | |
| 2008/0199526 A1 | 8/2008 | Poschalko et al. | |
| 2008/0213192 A1 | 9/2008 | Schlesinger et al. | |
| 2008/0213207 A1 * | 9/2008 | Lenzetti et al. | ................ 424/73 |
| 2009/0189090 A1 * | 7/2009 | Meyer et al. | .............. 250/461.1 |
| 2010/0316684 A1 | 12/2010 | Daniels | |

FOREIGN PATENT DOCUMENTS

| | | |
|---|---|---|
| CN | 102058488 A | 5/2011 |
| DE | 10015149 A1 | 12/2001 |
| EP | 1133983 A2 | 9/2001 |
| EP | 1508326 A1 | 2/2005 |
| JP | 2013170152 A | 9/2013 |
| WO | 9211839 A1 | 7/1992 |
| WO | 2010138266 A2 | 12/2010 |

OTHER PUBLICATIONS

E. Sagarin, Cosmetics Science and Technology, 2nd Edition, vol. 1, Wiley-Interscience (1972), Ch. 7, pp. 284-305.
Anonymous, "Water-Resistant Cosmetic Formulations Comprising a Hydrophobically Modified Vinylpyrrolidone Copolymer", IP.com, Aug. 2, 2011, IPCOM000209381D, 1-252.
Extended European Search Report in corresponding Application No. 13841081.6 dated Mar. 9, 2016.
International Search Report for International Application No. PCT/US2013/061299, dated Jan. 29, 2014.
Written Opinion of the International Searching Authority for corresponding application PCT/US2013/061299 dated Jan. 29, 2014.

* cited by examiner

*Primary Examiner* — Nannette Holloman

(57) ABSTRACT

In one aspect, the present invention is directed to formulations comprising at least one pressure generating vehicle along with at least one skincare active agent in a container such that the pressure generating vehicle would eject the formulation as foam, whipped cream or a similar form upon application of external pressure on the container.

7 Claims, No Drawings

FOAMING SKINCARE FORMULATIONS

FIELD OF THE INVENTION

This invention is directed to formulations and/or compositions, particularly lotion, cream or foam formulations, (in particular emulsion formulations) that are held under pressure. The subject invention is also directed to lotion formulations containing a pressure generating vehicle along with at least one recognized skin care active agent in a container or device such that the pressure generating vehicle would eject the formulation as foam, whipped cream or a similar form, upon application of external pressure on the container or device. The pressure generating vehicle is present in the device in sufficient amounts and pressure to mix with the ejecting formulation to form a foam, whipped cream or similar form or consistency.

BACKGROUND OF THE INVENTION

The invention relates to formulations which when dispensed from a device under pressure deposit lotion, cream, spray, ointment, gel or foam on the skin that exhibits a unique texture and appearance, spread easier and rubs in faster to provide an improved feel on the wearer's skin and thereby enhance the entire application experience of the user compared with conventional lotions, foams or mousses. Formulations that relate to the invention include formulations that are applied topically to skin that help repair and maintain skin's condition or that prevent damage from exposure to environmental insults, such as solar ultraviolet radiation, pollutants, excessively dry, cold or moist climates and the like.

The invention also relates to formulations which when deposited on skin from the pressurized device create an appearance and texture that reinforces attributes of softness and gentleness that are especially important to users who require relief from sensitive skin or from skin which is otherwise dry, inflamed, itchy or painful. When skin is compromised, it is frequently recommended that topical products be applied multiple times over the course of a day, so products that visually reinforce a product's skin benefits by its appearance can also help users comply with the need to make multiple applications during the day.

The invention also relates to formulations applied topically to skin for the purposes of protecting, repairing and maintaining skin health and include inter alia sunscreens, moisturizers, skin protectants and therapeutic emollient-based products.

There still exists a need for a skincare formulation that is easily applied to the skin of the user, and has a good texture and "feel" on the skin of the users. The product(s) of the present invention satisfy that need by having a very desirable "dry" and/or less greasy feel as it is being applied.

Yet another area where the present invention is applicable is sunscreen technology. Thus, the invention also relates to formulations that are applied to the skin to reduce the amount of solar ultraviolet radiation received by the skin. More particularly, the invention relates to formulations that impart several beneficial properties to topical formulations, including inter alia, ease of topical application, faster spreading, quick absorbance and a skin feel that is less greasy. A non-limiting example would be sunscreens. In the case of sunscreen, for example, it is now generally recognized that exposure to solar radiation can have adverse health consequences, sometimes not appearing until several years following the exposure. Of course, the immediately appearing sunburn from an overexposure can itself be a serious acute health problem.

Many products are available to reduce the amount of solar ultraviolet radiation received by the skin during exposure to the sun's rays. Typical product formulations are lotions, creams, ointments, sprays or gels containing chemical and/or physical barriers to ultraviolet transmission. These vary considerably in their abilities to protect the skin against the physical and biochemical effects of ultraviolet radiation. Many conventional cosmetic cream and lotion compositions are described, for example, in Sagarin, *Cosmetics Science and Technology*, 2nd Edition, Volume 1, Wiley Interscience (1972), and *Encyclopedia of Chemical Technology*, Third Edition, Volume 7.

Earlier sunscreen formulations were designed to protect against sunburn from a limited solar exposure period, while transmitting sufficient radiation to permit skin tanning. However, the current focus is on eliminating as much ultraviolet radiation exposure as possible, it being recognized that skin tanning, while aesthetically pleasing to some, is a clear indication of tissue damage from overexposure to solar radiation. It has been recently discovered that any amount of unprotected exposure can potentially cause immune system suppression and lead to future health problems, such as skin carcinomas and other dermatological disorders.

The SPF ("Sun Protection Factor") rating system has been developed to provide consumer guidance in selecting suitable sunscreens for any given outdoor activity. In general, the SPF number approximately corresponds to the multiple of time during which the properly applied sunscreen will prevent obvious reddening of the skin, over the exposure time that causes unprotected skin to exhibit reddening. Thus, if an SPF 8 sunscreen formulation has been properly applied, a person should be able to remain in the sun without visible effects for eight times the usual unprotected duration. Of course, the duration of unprotected exposure which produces a visible effect on the skin varies from one individual to another, due to differences in their skin cells. Currently popular are high-SPF "sunblocker" products, having SPF values of at least 30.

A sunscreen product that has been available for several years and sold by MSD Consumer Care, Inc., Memphis, Tenn., U.S.A., is COPPERTONE® SPORT® SPF 30 lotion. But there still exists a need for a sunscreen formulation that is easily applicable to the skin of the user, has a good texture and "feel" on the skin of the users. The product of the present invention satisfies that need by having a very desirable "dry" and/or "less greasy" feel as it is being applied.

In sunscreens, currently the FDA recommends reapplication of sunscreens after 2 hours. By having a very desirable and appealing feel, the inventive formulation may improve consumer compliance in that regard.

SUMMARY OF THE INVENTION

The present invention provides a skincare formulation for topical application in a device, the formulation comprising at least one recognized skincare active agent, and at least one pressure generating vehicle. The pressure generating vehicle is present in the device in sufficient amounts and pressure to mix with the ejecting formulation to form a foam, whipped cream or similar form or consistency.

The present invention provides a skincare formulation for topical application, the formulation comprising at least one recognized skincare active agent, emulsifying agent and at least one pressure generating vehicle.

The present invention provides a skincare formulation for topical application, the formulation comprising at least one recognized skincare active agent, a thickening agent, an emulsifying agent, and at least one pressure generating vehicle.

The invention also provides a skincare formulation comprising an oil-in-water emulsion formulation, the formulation comprising a nonaqueous phase, an aqueous phase, an oil-in-water emulsifying agent, a thickening agent, at least one skincare active agent, and at least one pressure generating vehicle.

The invention also provides a skincare formulation comprising a water-in-oil emulsion formulation, the formulation comprising a non-aqueous phase, an aqueous phase, water-in-oil emulsifying agent, a thickening agent, at least one skincare active agent and at least one insect repellant active agent, and at least one pressure generating vehicle.

The present invention provides a sunscreen formulation for topical application, the formulation comprising at least one recognized sunscreen active agent, and at least one pressure generating vehicle.

The present invention also provides a formulation for sunscreen application in a device, the formulation comprising at least one recognized sunscreen active agent, a thickening agent, and at least one pressure generating vehicle. The pressure generating vehicle is present in the device in sufficient amounts and pressure to mix with the ejecting formulation to form a foam, whipped cream or similar form or consistency.

The present invention also provides a formulation for sunscreen application, the formulation comprising at least one recognized sunscreen active agent, a thickening agent, an emulsifying agent, and at least one pressure generating vehicle.

The invention also provides a sunscreen formulation comprising an oil-in-water emulsion formulation, the formulation comprising a nonaqueous phase, an aqueous phase, an oil-in-water emulsifying agent, a thickening agent, at least one sunscreen active agent, and at least one pressure generating vehicle.

The invention also provides a sunscreen formulation comprising a water-in-oil emulsion formulation, the formulation comprising a non-aqueous phase, an aqueous phase, water in oil emulsifying agent, a thickening agent, at least one sunscreen active agent and at least one insect repellant active agent, and at least one pressure generating vehicle.

The formulations of the present invention exhibit ease of application including, for example, single handed application and single handed spreading on the skin of the user.

The inventive formulations of the present invention exhibit improved texture and feel on the wearer's skin.

DETAILED DESCRIPTION OF THE INVENTION

Names given to chemical substances herein generally are either accepted chemical names, or are trade organization or regulatory agency approved names such as CTFA Adopted Names as listed in J. A. Wenninger et al., Eds., *CTFA International Cosmetic Ingredient Dictionary*, Eighth Ed. and Tenth Ed., The Cosmetic, Toiletry and Fragrance Association, Washington, D.C., 1997 and 2000, respectively.

In this application, the term "percent" shall mean percent by weight unless the context clearly indicates otherwise.

The term "pressure generating vehicle" refers to a chemical component or components which generate pressure, e.g., compressed gas, while inside an enclosed device or container (such as a can, for example), and get released upon application of external pressure on the device (e.g., by way of a valve, actuator or similar such mechanism), while at the same time accompanying any other ingredients or formulation that is dispensed or expelled from inside the device. Non-limiting examples of such pressure generating vehicles are compressed gases/propellants and liquid propellants such as, for example, $CO_2$, propane, butane, isobutane, dimethyl ether, nitrous oxide and the like, and suitable blends of such propellants. When the valve is opened by applying an external pressure, the formulation or ingredients in the device are dispensed in a 'whipped' form or a foamy form, infused with bubbles (of $CO_2$ or other compressed gas/propellant as stated above), creating a unique texture of the formulation and "feel" on the wearer's skin.

For the purposes of this invention, the terms "external pressure" and "external force" are interchangeable regarding their intended meaning. Similarly, the terms "internal pressure" and "internal force" are interchangeable regarding their intended meaning.

The present invention offers a number of unique benefits for a skincare product (as well as thick lotion, cream, ointment and the like). Skincare formulations are typically greasy, heavy lotions that can be difficult to dispense from a traditional lotion package, cumbersome to spread across the skin, and they can leave a greasy residue on hands and skin that makes the experience less enjoyable. Many skin care products, especially for dry, chapped skin, have heavy greasy aesthetics, petrolatum-containing formulations being a prime example. Non-limiting examples of other skincare products that are likely to be benefit from the present invention include those associated with diaper rash, products that help with psoriasis and eczema, and the like. The formulations are also applicable to petrolatum-containing formulations, mineral oil-containing formulations, dimethicone-containing formulations as well as others that are generally recognized and known in the industry.

In one embodiment, the formulation dispenses in a continuous stream when an external pressure is applied to the device, such as by depressing the valve/actuator, thereby eliminating the need to squeeze and shake the formula out of a bottle or tube.

In another embodiment, the present invention operates as a "one-touch" delivery system; in such system, the user will hold down the actuator until the desired amount of formulation is dispensed.

In another embodiment, the present invention offers a continuous delivery system for skincare applications. Traditionally, "continuous delivery" is typically offered as a spray product and has been very successful due to the ease and speed that it provides for sunscreen application. Many consumers, however, prefer lotions/gels over sprays and would benefit from a continuous delivery mechanism. The present invention offers such an advantage.

In another embodiment, the inventive formulation dispenses in a light 'whipped' form, infused with tiny bubbles that make the texture of the formulation lighter, smoother and easier to spread across the skin. This texture also makes the formulation feel less greasy and more aesthetically pleasing on hands and skin, leaving a 'sumptuous' feel with a sunscreen during application. This formulation spreads quickly and disappears rapidly as the user rubs the formulation into the skin. Such a formulation may even prevent excess application of the agent and may offer ecological advantages.

In another embodiment, the present invention offers an easier, faster, smoother, and less greasy skincare formulation than a traditional formulation.

For purposes of the present invention, a "skincare active agent" shall include all of those materials which are regarded as acceptable for use as active skin-protecting ingredients. Approval by a regulatory agency may sometimes be required for inclusion of active agents in formulations intended for human contact including but not limited to sunscreen active ingredients or petrolatum, white petrolatum, mineral oil, and dimethicone as skin protectants, as well as agents used as self-tanners or for diaper rash treatment and the like. Those sunscreen active agents which have been or are currently approved for sunscreen use in the United States and elsewhere include, without limitation, paraaminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, octisalate, sulisobenzone, trolamine salicylate, titanium dioxide and zinc oxide, diethanolamine methoxycinnamate, digalloyl trioleate, ethyl dihydroxypropyl PABA, glyceryl aminobenzoate, lawsone with dihydroxy acetone, red petrolatum and the like. Several other sunscreen active ingredients are accepted for use in other countries. Some non-limiting examples from outside the U.S. include Tinosorb M, Tinosorb S, Uvinul T-150, UVA sorb HEB, Uvinul A Plus, Neo Heliopan AP, Neo Heliopan MBC, and the like. It is typical to use combinations of two or more skincare active agents in a formulation. Preferably, the amount of skincare active agent or agents is present in an amount that is consistent with the FDA guidelines. The use of a combination of active agents is especially true for sunscreen formulations in order to achieve higher levels of ultraviolet absorption or to provide useful absorption over a wider range of ultraviolet wavelengths than can be the case with a single active component. Preferably, the sunscreen active agent or agents is present in an amount that is consistent with the FDA sunscreen monograph for sunscreen active agent or agents that are believed to provide the requisite SPF in accordance with the FDA monograph for such sunscreens. Other skin care active agents include sunless tanning active agents, skin protectant active agent emollients, insect repelling agents, and the like.

The pressure generating vehicle can be formulated inside the device in a variety of ways, depending upon the nature of the component or components that form the pressure generating vehicle. The vehicle, while acting as pressure-generator, is a gas, even though it may have been packaged as, for example, a gas, a liquid or a solid. Non-limiting examples of the gas are carbon dioxide ($CO_2$), nitrous oxide ($N_2O$) and the like. Thus, for example, if the vehicle is carbon dioxide, the carbon dioxide can be 'derived' inside the sealed pressurized container in several ways. For example, the gas could be pumped into the container, or it could be added into the ingredients as "dry ice", or it could be derived or generated in situ via the chemical reaction of a suitable base with a suitable acid. In the case of "pumped in" or "dry ice", the gas is already present as $CO_2$. In the case of generation in situ via the chemical reaction of a base with an acid, the gas is generated when the acid and the base mix. In either case, when the valve or actuator or similar equipment on the device is depressed, this gas escapes the container along with and propelling the skincare formulation, creating a whipped consistency. The pressure generating vehicle is present in sufficient amounts to mix with the ejecting skincare formulation to form a foam, whipped cream or similar form and texture.

If generating the gas by chemical reaction between a base and an acid, non-limiting examples of suitable bases include sodium bicarbonate, sodium carbonate, potassium bicarbonate, potassium carbonate and the like. Non-limiting examples of suitable acids include acetic acid, citric acid and the like. Sodium bicarbonate with citric acid is a suitable combination. Because the components are being combined inside of the sealed container (device), the gas produced during the reaction is trapped which pressurizes the container. When the valve or actuator on the device is depressed, this gas escapes the container along with the skincare formulation, creating a whipped consistency.

There are a number of ways to combine the sodium bicarbonate and citric acid. In an illustrative way, the sodium bicarbonate is first combined with the skincare formulation (phase one) and then placed inside the device. Citric acid is then made into an aqueous solution (phase two) and carefully added on top. The vessel is sealed and then shaken to combine the two phases. The gas produced pressurizes the vessel.

In an alternative (reverse) way, the citric acid is first combined with the skincare formulation (phase one) and then placed inside the device. Sodium bicarbonate is then made into an aqueous solution (phase two) and carefully added on top. The vessel is sealed and then shaken to combine the two phases. The gas produced pressurizes the vessel.

It would also be possible to create this effect using a two chambered system where the two phases are combined at the point of use causing the formulation to begin foaming as it leaves the valve of the container. Such alternative designs are well known to the people skilled in the art.

One advantage of the inventive system is that the gas introduced or produced may be non-flammable.

The pressure generating vehicle is generally present in about 0.1 to about 80 wt % in the formulation as the formulation is ejected from the device. The pressure generating vehicle is selected from a gas, such as gaseous propellant, a liquid, such as a liquid propellant or a blend of gas and liquid. As used herein, a gaseous propellant is also a compressed gas, such as $CO_2$ and the like. As used herein, a liquid propellant is also a liquefied gas, such as isobutane and the like.

In some embodiments, for example, where gaseous propellant is used, the pressure generating vehicle is present from about 0.1 to about 50 wt %. In another embodiment, the gaseous propellant is present from about 0.1 to about 30 wt %. In another embodiment, the gaseous propellant is present from about 0.1 to about 15 wt %. In a further embodiment, the gaseous propellant is present from about 0.1 to about 10 wt %. In a preferred embodiment, the gaseous propellant is present from about 0.1 to about 5 wt %. Typically, when the pressure generating vehicle is a gaseous propellant, about 3 to about 5 wt % is present in the formulation.

In some embodiments, where liquid propellant is used, the pressure generating vehicle is present from about 0.1 up to about 60 wt %. %. In another embodiment, the liquid propellant is present from about 0.1 to about 40 wt %. In another embodiment, the liquid propellant is present from about 0.1 to about 30 wt %. In a further embodiment, the liquid propellant is present from about 0.1 to about 20 wt %. In a preferred embodiment, the liquid propellant is present from about 10 to about 30 wt %. Typically, when the pressure generating vehicle is a liquid propellant, about 15 to about 30 wt % is present in the formulation In some other embodiments, where blends of both gaseous and liquid propellants are used, the pressure generating vehicle is generally present up to about 15 wt % for the gaseous propellant and up to about 40 wt % for the liquid propellant, preferably up to about 10 wt % for the gaseous propellant and up to about 30 wt % for the liquid propellant, more preferably up to about 5 wt % for the gaseous propellant and up to about 20 wt % for the liquid propellant, and typically up to about 3 wt % for the gaseous propellant and up to about 20 wt % for the liquid propellant.

The term "emulsion" shall be used herein to identify oil-in-water (o/w) or water in oil (w/o) type dispersion formulations intended for application to the skin, particularly lotions and creams providing cosmetic or therapeutic benefits. The emulsions may contain any of a number of desired "active" ingredients, including skin colorants, drug substances (such as anti-inflammatory agents, antibiotics, topical anesthetics, antimycotics, keratolytics, etc.), skin protectants or conditioners, humectants, ultraviolet radiation absorbers and the like, depending on the intended uses for the formulations.

Suitable emulsifiers for one aspect of the invention are those known in the art for producing oil-in-water type emulsions. An aqueous external phase is preferred by many people for skin contact, since it is not as likely to produce an oily or greasy sensation when it is being applied, as is an emulsion having an oil external phase. The typical oil-in-water emulsifier has a hydrophilic-lipophilic balance (frequently abbreviated as "HLB") value greater than about 9, as is well known in the art; however, this "rule" is known to have numerous exceptions. The chosen emulsifier, depending upon its chemical nature, will be a component of either the oil or aqueous phase or both, and assists with both the formation and the maintenance, or stability, of the emulsion.

Although specific suppliers of commercially available ingredients may be listed herein, it is understood that these products may be available from additional suppliers and that the instant invention is not limited to only that ingredient from the specifically cited supplier. Rather the supplier is being provided as an example of what is commercially available.

Non-limiting examples of suitable emulsifiers or surfactants include pharmaceutically acceptable, non-toxic, non-ionic, anionic and/or cationic surfactants. Examples of suitable non-ionic surfactants include glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylene fatty alcohol ethers such as polyoxyethylene (20) stearyl ether, polyoxyethylene sorbitan fatty acid esters such as polyoxyethylene sorbitan monostearate, sorbitan esters such as sorbitan monostearate, alkyl glycosides such as cetearyl glucoside, fatty acid ethanolamides and their derivatives such as the diethanolamide of stearic acid, Prolipid and the like An example of a suitable Prolipid is Prolipid 141 which lists behenyl alcohol, glyceryl stearate, palmitic acid, stearic acid, myristyl alcohol, lauryl alcohol, cetyl alcohol and lecithin as its ingredients in its Formula Data Sheet. Examples of suitable anionic surfactants are soaps including alkali soaps, such as sodium, potassium and ammonium salts of aliphatic carboxylic acids, usually fatty acids, such as sodium stearate. Organic amine soaps include organic amine salts of aliphatic carboxylic acids, usually fatty acids, such as triethanolamine stearate. Metallic soaps include salts of polyvalent metals and aliphatic carboxylic acids, usually fatty acids, such as aluminum stearate. Other classes of suitable anionic surfactants include sulfated fatty acid alcohols such as sodium lauryl sulfate, sulfated oils such as the sulfuric ester of ricinoleic acid disodium salt, and sulfonated compounds such as alkyl sultonates including sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such a sodium isopropyl naphthalene sulfonate, petroleum sultonate such as aryl naphthalene with alkyl substitutes. Examples of suitable cationic surfactants include amine salts such as octadecyl ammonium chloride, quaternary ammonium compounds such as benzalkonium chloride. Non-limiting examples of emulsifiers include a mixture of cetearyl glucoside and cetearyl alcohol, available under the trade name Emulgade PL68/50 from Henkel KGaA, and PEG 30 dipolyhydroxy stearate, available under the trade name Arlacel 135 from ICI. Also preferred are various $C_{12-15}$, $C_{12-16}$ and $C_{14-15}$ alcohols available from various manufacturers, and Ceteareth 2, 10, 18, 22, Ceteth-1 and 20, cetyl dimethicone copolyol, and cetyl phosphate, glyceryl stearate, Oleth 3 and 10, polyglyceryl 3 methylglucose distearate sorbitan isostearate, steareth 2, 10, and/or 20.

Suitable emulsifiers for another aspect of the invention are those known in the art for producing water-in-oil type emulsions. Non-limiting examples of some suitable water-in-oil emulsions include SIMALINE WO (PEG-30 Dipolyhydroxystearate; available from Seppic), FLUIDANOV 20X (Octyldodecanol & Octyldodecyl Xyloside; available from Seppic), ES-5300 (Lauryl PEG-10 Tris(trimethylsiloxy)silylethyl Dimethicone; available from Dow Corning), Abil EM90 (Cetyl PEG/PPG-10/1 Dimethicone; available from Evonik) and Abil WE09 (Polyglyceryl-4 Isostearate and Cetyl PEG/PPG-10/1 Dimethicone and Hexyl Laurate; available from Evonik). The typical water-in-oil emulsifier has a HLB value of about 4 to about 6, however, this "rule" is also known to have numerous exceptions.

It may be advantageous to incorporate thickening agents, such as, for instance, Carbopol Ultrez, Carbopol ETD 2001, available from the B. F. Goodrich Co, Abil Wax 9801, a surfactant available from Gold Schmidt, Alginic Acid, available from Kelco, cellulose gum, available from TIC Gums, ammonium acrylates copolymer, ammonium polyacryloyl dimethyl taurate, bentonite available from Southern Clay, guar hydroxypropyltrimonium chloride available from Henkel, hydroxy propylprocellulose available from Aqualon, magnesium aluminum silicate, available from Salomon, potassium alginate available from Kelco, beeswax available from Strah & Pitsch, and behenyl alcohol available from Nikko.

Insect repelling components are also a desirable ingredient in certain skincare and sunscreen formulations, if the formulations are to be used by persons engaged in outdoor activities. The most widely used insect repelling agent for personal care products is N,N-Diethyl-m-toluamide, frequently called "DEET" and available in the form of a concentrate containing at least about 95 percent DEET. Other synthetic chemical repellents include dimethyl phthalate, ethyl hexanediol, indalone, di-n-propylisocinchoronate, bicycloheptene, dicarboximide, IR3535 (3-[N-Butyl-N-acetyl]-aminopropionic acid, ethyl ester; available from Merck KGaA)) and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the skincare or sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

The compositions/formulations of the present invention may contain a wide range of additional, optional components. The CTFA Cosmetic Ingredient Handbook, Seventh Edition, 1997, and the Eighth Edition, 2000, which are both incorporated by reference herein in their entirety, describe a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, cryoprotectants, film stabilizers, denaturants, drug astringents, external analgesics, film formers, fragrance components, humectants, pacifying agents, pH adjusters, plasticizers, preservatives, propellants, reducing agents, skin bleaching agents, skin-conditioning agents (emollients, humectants, miscellaneous, and occlusive), skin protectants, solvents, SPF enhancers/boosters, foam boosters, hydrotropes, solubilizing agents, suspending agents (nonsurfactant), sunscreen agents, ultraviolet light absorbers, waterproofing agents, and viscosity increasing agents (aqueous and nonaqueous).

An emollient is a substance which helps to smooth and soften the skin, and may also reduce its roughness, cracking or irritation. Non-limiting examples of suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil. Preferably, the emollient is a cocoglyceride, which is a mixture of mono, di and triglycerides of cocoa oil, sold under the trade name of Myritol 331 from Henkel KGaA, or Dicaprylyl Ether available under the trade name Cetiol OE from Henkel KGaA or a $C_{12}$-$C_{15}$ Alkyl Benzoate sold under the trade name Finsolv TN from Finetex. One or more emollients may be present ranging in amounts from about 1 percent to about 10 percent by weight, preferably about 5 percent by weight. Another suitable emollient is DC 200 Fluid 350, a silicone fluid, available Dow Corning Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linotenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can be optionally included in the formulation.

The compositions of the invention can further comprise skin protectant active agents. Suitable examples include (with preferred weight percent ranges), Allantoin (0.5 to 2 percent); Aluminum hydroxide gel (0.15 to 5 percent), Calamine (1 to 25 percent); Cocoa butter (greater than 50 percent); Cod liver oil (5 to 14 percent); Colloidal oatmeal; Dimethicone (1 to 30 percent); Glycerin (20 to 45 percent); Hard fat (greater than 50 percent); Kaolin (4 to 20 percent); Lanolin (12.5 to 50 percent); Mineral oil (greater than 50 percent); Petrolatum (greater than 30 percent); Sodium bicarbonate; Topical starch (10 to 98 percent); White petrolatum (greater than 30 percent); Zinc acetate (0.1 to 2 percent); Zinc carbonate (0.2 to 2 percent); and Zinc oxide (1 to 25 percent).

Water is employed in amounts effective to form the emulsion. It is generally preferred to use water which has been purified by processes such as deionization or reverse osmosis, to improve the batch-to-batch formulation inconsistencies which can be caused by dissolved solids in the water supply. The amount of water in the emulsion or composition can range from about 15 percent to 95 weight percent.

A humectant is a moistening agent that promotes retention of water due to its hygroscopic properties. Suitable humectants include glycerin, polymeric glycols such as polyethylene glycol and polypropylene glycol, mannitol and sorbitol. Preferably, the humectant is glycerin, Sorbitol 70% USP or polyethylene glycol 400, NF. More preferably, the humectant is glycerin. One or more humectants can optionally be included in the formulation in amounts from about 1 percent to about 10 percent by weight, preferably about 5 percent by weight. Other suitable humectants include, inter alia, fructose, glucose, glycerin, lactic acid, PCA, potassium lactate and PCA, propylene glycol, sodium lactate and PCA.

A dry-feel modifier is an agent which when added to an emulsion, imparts a "dry feel" to the skin when the emulsion dries. Dry feel modifiers can include talc, kaolin, chalk, starches, zinc oxide, silicone fluids, inorganic salts such as barium sulfate, surface treated silica, precipitated silica, fumed silica such as an Aerosil (silica) available from Degussa Inc., DryFlo starch (aluminum starch octenylsucinate available from Akzo Nobel), and/or an epichlorohydrin cross-linked glyceryl starch, available from National Starch under the current tradename of Vulca 90 starch.

The present formulation may additionally contain waterproofing agents. A waterproofing or water resistance agent is a hydrophobic material that imparts film forming and waterproofing characteristics to an emulsion. A waterproofing agent that can be used in conjunction with the waterproofing agents of the present invention can be a copolymer of vinyl pyrollidone and eicosene and dodecane monomers such as the Ganex V 220, Ganex P-904 LC, and Ganex V 216 Polymers, respectively, available from ISP Inc. of Wayne, N.J. Still other suitable waterproofing agents include poly alfa olefin polymers, such as Performa V 825 available from New Phase Technologies and polyanhydride resin No. 18 available under the trade name PA-18 from Chevron. Additional examples of waterproofing agents are polyurethane polymers. Some such polymers are described, for example, in U.S. Pat. No. 7,097,828.

An antimicrobial preservative is a substance or preparation which destroys, prevents or inhibits the proliferation of, microorganisms in the sunscreen composition, and which may also offer protection from oxidation. Preservatives are frequently used to make self-sterilizing, aqueous based products such as emulsions. This is done to prevent the development of microorganisms that may grow in the product during the manufacture and distribution of the product and/or during use by consumers, who may further inadvertently contaminate the products during normal use. Typical preservatives include the lower alkyl esters of para-hydroxybenzoates (parabens), especially methylparaben, propylparaben, isobutylparaben and mixtures thereof, benzyl alcohol, phenyl ethyl alcohol and benzoic acid. The preferred preservative is available under the trade name of Germaben II from Sutton or a combination of chlorophenesin and benzyl alcohol. One or more antimicrobial preservatives can optionally be included in an amount ranging from about 0.001 to about 10 weight percent, preferably about 0.05 to about 1 percent.

An antioxidant is a natural or synthetic substance added to the sunscreen to protect from or delay its deterioration due to the action of oxygen in the air (oxidation) and to protect the skin from sun damage. Anti-oxidants prevent oxidative deterioration which may lead to the generation of rancidity and nonenzymatic browning reaction products. Typical suitable antioxidants include propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Oxynex (Oxynex ST liquid is a mixture of diethylhexyl syringylidenemalonate and caprylic/capric triglyceride), Vitamin A, Vitamin E and Vitamin C. One or more antioxidants can optionally be included in the composition in an amount ranging from about 0.001 to about 5 weight percent, preferably about 0.01 to about 0.5 percent.

Chelating agents are substances used to chelate or bind metallic ions, such as with a heterocyclic ring structure so that the ion is held by chemical bonds from each of the participating rings. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the composition in amounts ranging from about 0.001 to about 0.2 weight, percent preferably about 0.01% weight percent.

The inventive formulation may include foam stabilizers or foam stabilizing agents. There are many examples of such agents and means to achieve foam stability. Non-limiting examples of suitable foam stabilizers include the Avicels, Capmul S12L, Capmul S18L, Amilite GCK-12, Amadol CMA-2, Ampholak 7 CX-C, Ampholak X CO-30, Polyox WSR N-10, Amaranth S, Foam-Coll 5, Blanose 12M31XP, Genu carrageenan, Avanel S150CG and others. Avicel is an example that can be used in the formulation. For example, Avicel RC-591 is a mixture of cellulose gum and microcrystalline cellulose. Some foam stabilizers also help improve long term high temperature stability.

Fragrances are aromatic substances which can impart an aesthetically pleasing aroma to the skincare or sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. Both types are considered to be within the scope of the present invention.

A pH modifier is a compound that will adjust the pH of a formulation to a lower, e.g., more acidic pH value, or to a higher, e.g., more basic pH value. The formulations of the present invention may contain such pH modifiers as is necessary.

In an embodiment of the instant invention, an SPF enhancer or booster, including styrene/acrylates copolymer (such as Sunspheres PGL, commercially available from Dow Chemical) may be optionally added to the formulation.

The present formulation may be used as an after sun formulation. As used herein, an after sun emulsion formulation is defined as a formulation that can be administered after a user has been in the sun for any amount of time and is a formulation that provides a soothing or healing effect that is pleasant to the user. Such a formulation can contain, for instance, aloe vera, vitamins A and E, cooling agents, moisturizers, redness-reducing agents and the like.

The present formulation may be used as self-tanning composition or for sunless tanning. As used herein, the term "sunless-tanning" or "self-tanning compositions" refer to compositions which, when applied to human skin, impart thereto an appearance similar to that achieved by exposing the skin to natural or artificial sunlight. Examples of sunless tanning active agents are described in U.S. Pat. Nos. 6,482, 397, 6,261,541, and 6,231,837. Such sunless tanning compositions typically comprise, in addition to an artificial tanning effective amount of a self tanning agent, effective amounts of a composition coloring agent and a cosmetically acceptable carrier adapted for topical application to human skin. The self tanning agents can also include those compositions generally accepted in the art for application to human skin, and which, when so applied, react therein with amino acids so as to form pigmented products. Such reactions give the skin a brown appearance, similar to the color obtained upon exposing it to sunlight for periods of time sufficient to tan the skin. Suitable self tanning agents include, without limitation, alpha-hydroxy aldehydes and ketones, glyceraldehyde and related alcohol aldehydes, various indoles, imidazoles and derivatives thereof, and various approved pigmentation agents. Presently preferred herein as self tanning agents are the alpha-hydroxy aldehydes and ketones. Most preferably, the self tanning agent is dihydroxyacetone ("DHA"). Other suitable self tanning agents include, without limitation, methyl glyoxal, glycerol aldehyde, erythrulose, alloxan, 2,3-dihydroxysuccindialdehyde, 2,3-dimethoxysuccindialdehyde, 2-amino-3-hydroxy-succindialdehyde and 2-benzylamino-3-hydroxysuccindialdehyde.

The present invention is not dependent upon any particular formulation technique, it being recognized that the choice of specific formulation components may well make necessary some specific formulation procedure.

REPRESENTATIVE EXAMPLES

The invention will be further described by means of the following examples, which are further illustration purposes only and are not intended to limit the invention, as defined by the appended claims, in any manner.

Example 1. Skincare Formulation Containing $CO_2$

The following ingredients were taken in Parts A-F:

Part A contained USP Purified water (409.80 g) and Avicel RC-591 (20.0 g).

Part B contained Disodium EDTA (0.5 g), Ganex P-904 LC (2.0 g) and Sodium ascorbyl phosphate (0.1 g).

Part C contained Avobenzone (30.0 g), Oxybenzone (60.0 g), Prolipid 141 (50.0 g), Octocrylene (100.0 g), Octisalate (50.0 g) and Homosalate (150.0 g).

Part D contained Chlorphenesin (2.5 g), Vitamin E (DL-alpha tocopherol, 5.0 g), Benzyl alcohol (10.0 g), Oxynex ST (10.0 g), Butylene alcohol (40.0 g) and Vitamin A palmitate (0.1 g).

Part E contained Citric acid (30.0 g).

Part F contained 30.0 g. of sodium bicarbonate.

In a large container, the dry ingredients of Part A were mixed rapidly with the water of Part A until free from lumps. The ingredients of Part B were then added and mixed until dispersed and then it was heated to about 70-75° C. with mixing.

In a separate container, the ingredients of Part C were mixed together and heated to about 70-75° C. with mixing until dissolved. The heat was turned off and the ingredients of Part D were added to the dissolved Part C and mixed until the chlorphenesin was in solution. There was now an oil phase and an aqueous phase. The oil phase was added to the mixture containing Parts A and B and mixed until homogeneous. It was cooled to about 45° C. and the citric acid of Part E was added and mixed until homogeneous. This was Component A.

Separately sodium bicarbonate of Part F formed Component B.

Both components A and B were placed in suitable containers and sealed tightly. The containers were selected such that when pressurized, the components of both containers would mix forming $CO_2$ which pressurizes the formulation as a whipped lotion.

Alternately, the two components A and B were carefully mixed in a suitable single container which was then sealed, trapping the $CO_2$ generated within the container. When pressed, the $CO_2$ helped propel the formulation as a whipped lotion.

Example 2. Use of Dry Ice Instead of Bicarbonate and Citric Acid

For the dry ice example, the formulation of Example 1 (without the citric acid and bicarbonate) was prepared as a single component and placed in a pressurizable container and then dry ice was added at about 1.2% by weight of the formulation. At this point the vessel was quickly sealed before the dry ice had a chance to sublime. Citric acid may be included in the formulation without any bicarbonate.

Example 3: Use of Gaseous $CO_2$ as the Propellant for Pressure Generation

A formulation containing the following ingredients was prepared (all amounts are wt/wt %):
Water: 45.026
Homosalate: 14.361
Octocrylene: 9.574
Oxybenzone: 5.744
Octisalate: 4.787
Prolipid 141: 4.787
1,3-Butylene glycol: 3.830
Spherol LC KAA: 2.961
Avobenzone: 2.872
Avicel RC-591: 1.915
$CO_2$ propellant: 1.300
Benzyl alcohol: 0.957
Oxynex ST: 0.957
Vitamin E: 0.479
Chlorphenesin: 0.191
Ganex P-904: 0.191
Disodium EDTA: 0.048
Sodium ascorbyl phosphate: 0.010
Vitamin A palmitate: 0.010

The formulation was placed in a suitable container that could be pressurized to activate the release of the formulation as whipped concentrate.

Example 4: Formulation Containing Petrolatum and Gaseous $CO_2$

A formulation containing the following ingredients was prepared (all amounts are wt/wt %):
Water: 56.308
Perfecta White Petrolatum: 29.610
Prolipid 141: 4.935
1,3-Butylene glycol: 3.948
Avicel RC-591: 1.974
$CO_2$ propellant: 1.300
Benzyl alcohol: 0.987
Vitamin E: 0.493
Chlorphenesin: 0.197
Ganex P-904: 0.197
Disodium EDTA: 0.050

The formulation was placed in a suitable container that could be pressurized to activate the release of the formulation as whipped concentrate.

Example 5: P Formulation Containing Petrolatum, Tegocare and Gaseous $CO_2$

A formulation containing the following ingredients was prepared (all amounts are wt/wt %):
Water: 49.044
Perfecta White Petrolatum: 29.610
Tegosoft CT J: 4.935
Sorbitol 70% solution: 3.948
Prolipid 141: 2.961
Tegocare 450: 2.961
Avicel RC-591: 1.974
$CO_2$ propellant: 1.300
Benzyl alcohol: 0.888
Citric acid: 0.691
White Wax: 0.494
Tegosoft CT J: 0.494
Chlorphenesin: 0.296
Xanthan Gum: 0.296
Phytoconcentrole Rose: 0.108

The formulation was placed in a suitable container that could be pressurized to activate the release of the formulation as whipped concentrate.

Example 6: Formulation Containing In Situ Generated $CO_2$ Held Under Pressure A formulation containing the following ingredients was prepared (all amounts are wt/wt %):
Water: 40.980
Homosalate: 15.000

Octocrylene: 10.000
Oxybenzone: 6.000
Octisalate: 5.000
Prolipid 141: 5.000
1,3-Butyleneglycol: 4.000
Avobenzone: 3.000
Citric acid: 3.000
Avicel RC-591: 2.000
Benzyl alcohol: 1.000
Oxynex ST liquid: 1.000
Vitamin E: 0.500
Chlorphenesin: 0.250
Ganex P-904: 0.200
Disodium EDTA: 0.050
Sodium ascorbyl phosphate: 0.010
Vitamin A palmitate: 0.010

All the above-noted ingredients were mixed in a suitable container after which sodium bicarbonate (3.000 wt/wt %) was added and sealed immediately trapping the $CO_2$ generated. The device could be pressurized to activate the release of the formulation as whipped concentrate.

Example 7: Use of Blend of Gaseous $CO_2$ and Liquid Propellant (Isobutane) as the Propellant for Pressure Generation A formulation containing the following ingredients was prepared (all amounts are wt/wt %):
Water: 34.803
Isobutane: 25.000
Homosalate: 11.100
Octocrylene: 7.400
Oxybenzone: 4.440
Octisalate: 3.700
Prolipid 141: 3.700
1,3-Butylene glycol: 2.960
Avobenzone: 2.220
Avicel RC-591: 1.480
$CO_2$ propellant: 1.000
Benzyl alcohol: 0.740
Oxynex ST: 0.740
Vitamin E: 0.370
Chlorphenesin: 0.148
Ganex P-904: 0.148
Disodium EDTA: 0.037
Sodium ascorbyl phosphate: 0.007
Vitamin A palmitate: 0.007

The formulation was placed in a suitable container being pressurized by the addition of the isobutane and $CO_2$ propellants to expel the formulation as a whipped concentrate.

Example 8: Use of Liquid Propellant A-31 (Isobutane) Only as the Propellant for Pressure Generation A formulation containing the following ingredients was prepared (all amounts are wt/wt %):
Water: 35.803
Isobutane: 25.000
Homosalate: 11.100
Octocrylene: 7.400
Oxybenzone: 4.440
Octisalate: 3.700
Prolipid 141: 3.700
1,3-Butylene glycol: 2.960
Avobenzone: 2.220
Avicel RC-591: 1.480
Benzyl alcohol: 0.740
Oxynex ST: 0.740
Vitamin E: 0.370
Chlorphenesin: 0.148
Ganex P-904: 0.148
Disodium EDTA: 0.037
Sodium ascorbyl phosphate: 0.007
Vitamin A palmitate: 0.007

The formulation was placed in a suitable container being pressurized by the addition of the isobutane to expel the formulation as a whipped concentrate.

Example 9. Example of Whipped Lotion for Skin Care

A. Lotion Composition

| Ingredient | % |
| --- | --- |
| Part A | |
| White petrolatum | 15.000 |
| Mineral oil | 6.000 |
| Ceteth-20 | 2.250 |
| Cetostearyl alcohol | 7.200 |
| Part B | |
| Water purified | 69.148 |
| Sodium phosphate monobasic monohydrate | 0.300 |
| Phosphoric acid | 0.002 |
| Chlorocresol | 0.100 |

1. The ingredients of Part A were added into a container, heated to 70° C. It was mixed until all the ingredients have melted and the mixture was uniform.
2. In a separate container large enough to hold the entire batch, the ingredients of Part B were added and heated to 70° C. It was mixed until all ingredients were solubilized and the mixture was homogeneous.
3. With mixing, the oil phase of Part A was added to the water phase of Part B. The agitation or mixing speed was increased sufficiently to achieve emulsification.
4. Mixing was continued while the batch cools to room temperature.
5. The cream was transferred to a suitable storage container.

B. Creation of Whipped Lotion

For $CO_2$ (or a similar propellant): The formulation was placed in a suitable container that could be pressurized to activate the release of the formulation as a whipped lotion with the aid of the propellant.

Example 10: A Lower Amount of Liquid Propellant A-31 (Isobutane) as the Propellant for Pressure Generation A formulation containing the following ingredients was prepared (all amounts are wt/wt %):
Water: 45.153
Isobutane: 10.000
Homosalate: 9.000
Sunspheres PGL: 7.200
Oxybenzone: 5.400
Octisalate: 4.050
Prolipid 141: 4.050
Dry-Flo Pure: 3.600
Octocrylene: 3.600
Avobenzone: 2.700

1,3-Butylene glycol: 2.250
Avicel RC-591: 0.900
Benzyl alcohol: 0.810
Ganex P-904: 0.720
Chlorphenesin: 0.243
Vitamin E: 0.225
Disodium EDTA: 0.090
Sodium ascorbyl phosphate: 0.009

The formulation was placed in a suitable container being pressurized by the addition of the isobutane to expel the formulation as a whipped concentrate.

What is claimed is:

1. A sunscreen formulation for topical application in a device, the formulation comprising
    a pressure generating vehicle and at least three sunscreen active agents, and wherein said pressure generating vehicle consists of nitrous oxide, and
        said pressure generating vehicle is present in said device in sufficient amounts and pressure suitable to expel said formulation in the form of foam or whipped cream upon application of external pressure on said device, and
    wherein the sunscreen active agents are selected from avobenzone, dioxybenzone, homosalate, octocrylene, octyl salicylate, oxybenzone, octisalate, titanium dioxide or zinc oxide.

2. The formulation of claim 1, wherein the formulation additionally contains a thickening agent.

3. The formulation of claim 2, wherein the formulation additionally contains an emulsifier.

4. The formulation of claim 1, wherein the nitrous oxide is present in an amount of about 0.1% to about 30% by weight.

5. The formulation of claim 4, wherein the nitrous oxide is present in an amount of about 0.1% to about 10% by weight.

6. The formulation of claim 2 additionally comprising one or more agents selected from the group consisting of an emollient, a humectant, a pH modifier, a colorant, and a foam stabilizer.

7. The formulation of claim 1 further comprising:
    octocrylene;
    octisalate;
    homosalate;
    avobenzone;
    oxybenzone;
    a foam stabilizer comprising a mixture of cellulose gum and microcrystalline cellulose; and
    an emulsifier mixture comprising a combination of emulsifiers selected from behenyl alcohol, glyceryl stearate, palmitic acid, stearic acid, myristyl alcohol, lauryl alcohol, cetyl alcohol and lecithin.

* * * * *

UNITED STATES PATENT AND TRADEMARK OFFICE
CERTIFICATE OF CORRECTION

PATENT NO. : 10,179,094 B2
APPLICATION NO. : 14/034802
DATED : January 15, 2019
INVENTOR(S) : Graham et al.

It is certified that error appears in the above-identified patent and that said Letters Patent is hereby corrected as shown below:

In the Specification
In Column 4, Line 36, delete "to be benefit" and insert -- to benefit --, therefor.
In Column 8, Line 7, delete "alkyl sultonates" and insert -- alkyl sulfonates --, therefor.
In Column 8, Line 8, delete "sodium N-methyl-N-oleyl laurate," and
insert -- sodium N-methyl-N-oleyl taurate, --, therefor.
In Column 8, Line 12, delete "petroleum sultonate" and insert -- petroleum sulfonate --, therefor.
In Column 8, Line 48, delete "guar hydroxpropyltrimonium chloride" and insert
-- guar hydroxypropyltrimonium chloride --, therefor.
In Column 8, Line 52, delete "Strah & Pitsch," and insert -- Strahl & Pitsch, --, therefor.
In Column 8, Line 65, delete "KGaA))" and insert -- KGaA) --, therefor.
In Column 10, Lines 51-52, delete "octenylsucinate" and insert -- octenylsuccinate --, therefor.
In Column 10, Lines 60-61, delete "vinyl pyrollidone" and insert -- vinylpyrrolidone --, therefor.
In Column 11, Line 19, delete "chlorophenesin" and insert -- chlorphenesin --, therefor.
In Column 14, Line 37, delete "P Formulation" and insert -- Formulation --, therefor.

Signed and Sealed this
Thirtieth Day of April, 2019

Andrei Iancu
*Director of the United States Patent and Trademark Office*